(12) United States Patent
Weissman et al.

(10) Patent No.: US 9,151,760 B2
(45) Date of Patent: Oct. 6, 2015

(54) ISOLATION AND USE OF MELANOMA CANCER STEM CELLS

(75) Inventors: Irving L. Weissman, Stanford, CA (US); Alexander D. Boiko, Menlo Park, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 628 days.

(21) Appl. No.: 13/498,876

(22) PCT Filed: Sep. 29, 2010

(86) PCT No.: PCT/US2010/050776
§ 371 (c)(1),
(2), (4) Date: May 23, 2012

(87) PCT Pub. No.: WO2011/041453
PCT Pub. Date: Apr. 7, 2011

(65) Prior Publication Data
US 2012/0225073 A1    Sep. 6, 2012

Related U.S. Application Data

(60) Provisional application No. 61/277,849, filed on Sep. 29, 2009.

(51) Int. Cl.
*A61K 39/395* (2006.01)
*A61P 35/00* (2006.01)
*A61K 38/02* (2006.01)
*G01N 33/574* (2006.01)
*C12N 5/095* (2010.01)
*A61K 47/48* (2006.01)

(52) U.S. Cl.
CPC ...... *G01N 33/5743* (2013.01); *A61K 39/39558* (2013.01); *A61K 47/48538* (2013.01); *A61K 47/48569* (2013.01); *A61K 47/48676* (2013.01); *C12N 5/0695* (2013.01)

(58) Field of Classification Search
None
See application file for complete search history.

(56) References Cited

PUBLICATIONS

Wheeler, Salud p'ublica de M'exico, 1997, vol. 39, pp. 283-287.*
Efferson et al (Anticancer research, 2005, vol. 25, pp. 715-724).*
Bachman et al (Journal of Immunology, 2005, vol. 175, pp. 4677-4685).*
Robinson, PLoS Biology, 2004, vol. 1, pp. 0018-0020.*
Reed et al, American Journal of Pathology, 1999, vol. 155, pp. 549-555.*
Marchetti et al (Journal of Cellular Biochemistry, 2004, vol. 91, pp. 206-215).*
Abbott; et al. "Exploiting the convergence of embryonic and tumorigenic signaling pathways to develop new therapeutic targets", Stem Cell Rev (Jan. 2007), 3(1):68-78.
Cedervall; et al. "Species-specific in vivo engraftment of the human BL melanoma cell line results in an invasive dedifferentiated phenotype not present in xenografts", Cancer Res (May 2009), 69(9):3746-3754.

* cited by examiner

*Primary Examiner* — Karen Canella
(74) *Attorney, Agent, or Firm* — Bozicevic, Field & Francis LLP; Pamela J. Sherwood

(57) ABSTRACT

A set of markers for melanoma cancer stem cells are provided. The cells can be prospectively isolated or identified from primary tumor samples, and possess the unique properties of cancer stem cells in functional assays for tumor initiation, cancer stem cell self-renewal and differentiation. In addition, cancer stem cells can be used as a predictor for disease progression. The CSC have the phenotype of being positive for expression CD271.

15 Claims, 6 Drawing Sheets

FIG. 2b

| Patient | 10 | | 10² | | 10³ | | 2×10³ | | (3-5)×10³ | | 10⁴ | | 2×10⁴ | | 10⁵ | |
|---|---|---|---|---|---|---|---|---|---|---|---|---|---|---|---|---|
| | Lin- - | + | Lin- - | + | Lin- - | + | Lin- - | + | Lin- - | + | Lin- - | + | Lin- - | + | Lin- - | + |
| Mel114 | 0/2 0/2 | 0/4 | 0/2 0/2 | 1/2 | 0/2 0/2 | 2/2 | | | 0/2 0/2 | 1/2 | 0/2 0/2 | 2/2 | | | 2/2 | 0/2 |
| Mel425 | | | | | | | 1/5 | 4/5 | | | | 1/1 | | | | |
| Mel826 | | | | 0/1 | | 1/1 | 0/2 | 2/2! | 1/2 | 1/1*! | 0/1 | 1/1 | | 0/1* | | |
| Mel210 | | | 0/2 | 0/2 | 0/1* | 1/1* | | | | | | | | | | |
| Mel1119 | 0/2 | | 0/2 | 0/2 | 0/2 | 0/2 | | 4/4! | | | | | | | | 1/2 |
| Mel213 | 0/2 | 0/2 | 0/2 | 0/2 | 1/2 | 2/2 | 0/4 | | 1/2 | 1/2! | | | | | | |
| Total | 0/6 | 0/4 | 0/7 | 4/7 | 1/6 | 6/7 | 1/11 | 10/11 | 0/2 2/6 | 3/5 | 0/4 0/3 | 3/3 | 0/1 | | 3/4 | 0/2 |

(-) CD271- cells injected; (+) CD271+ cells injected; (!) metastatic lesions; (*) humanized mouse system

FIG. 2c

| | 10-10² | | 10³ - 2×10³ | | 3×10³-10⁴ | | 2×10⁴-10⁵ | |
|---|---|---|---|---|---|---|---|---|
| | Lin- - | + | Lin- - | + | Lin- - | + | Lin- - | + |
| Direct from patients | 0/12 0/11 | 4/11 | 1/8 1/18 | 16/18 | 0/6 2/9 | 6/8 | 3/4 0/3 | NA |
| | (p <0.033) | | (p <0.0001) | | (p <0.015) | | | |

Total: Lin-    5/29     (~17.2%)
CD271-  3/40     (~7.5%)
CD271+  25/37    (~67.5%)

ISOLATION AND USE OF MELANOMA CANCER STEM CELLS

FEDERALLY SPONSORED RESEARCH AND DEVELOPMENT

This invention was made with Government support under contracts CA126252 and CA139490 awarded by the National Institutes of Health. The Government has certain rights in the invention.

BACKGROUND

A tumor can be viewed as an aberrant organ initiated by a tumorigenic cancer cell that acquired the capacity for indefinite proliferation through accumulated mutations. In this view of a tumor as an abnormal organ, the principles of normal stem cell biology can be applied to better understand how tumors develop and disseminate. Many observations suggest that analogies between normal stem cells and tumorigenic cells are appropriate. Both normal stem cells and tumorigenic cells have extensive proliferative potential and the ability to give rise to new (normal or abnormal) tissues. Tumorigenic cells can be thought of as cancer stem cells (CSC) that undergo an aberrant and poorly regulated process of organogenesis analogous to what normal stem cells do. Both tumors and normal tissues are composed of heterogeneous combinations of cells, with different phenotypic characteristics and different proliferative potentials.

Cancer stem cells are believed to be a small fraction of tumor cells with stem cell-like properties, which initiate and maintain neoplastic clones. These cells have the ability to self-renew, but also give rise to progenitors that yield phenotypically diverse cancer cells but with lower tumorigenic potential. This subpopulation of stem-like cells should be highly efficient at tumor formation as compared to tumor cells that are not cancer stem cells.

Cancer stem cells (CSCs) have now been identified in a wide variety of cancers including melanomas, medulloblastomas, colon, liver, lung, prostate, breast and ovarian tumors. While CSCs do not necessarily arise from normal stem cells, they have frequently been isolated by using markers found in normal stem cells. For example, the marker CD133 has been used to identify normal adult hematopoietic and neural stem cells. CD133 has now been successfully used to enrich for CSCs from melanoma, medulloblastoma, colon and prostate tumors.

The presence of cancer stem cells has profound implications for cancer therapy. At present, all of the phenotypically diverse cancer cells in a tumor are treated as though they have unlimited proliferative potential and can acquire the ability to metastasize. For many years, however, it has been recognized that small numbers of disseminated cancer cells can be detected at sites distant from primary tumors in patients that never manifest metastatic disease. One possibility is that most cancer cells lack the ability to form a new tumor such, that only the dissemination of rare cancer stem cells can lead to metastatic disease. Hence, the goal of therapy must be to identify and kill this cancer stem cell population.

Existing therapies have been developed largely against the bulk population of tumor cells, because the therapies are identified by their ability to shrink the tumor mass. However, because most cells within a cancer have limited proliferative potential, an ability to shrink a tumor mainly reflects an ability to kill these cells. Therapies that are more specifically directed against cancer stem cells may result in more durable responses and cures of metastatic tumors.

It is highly desirable to be able to identify these cancer stem cells using specific markers, and then use these markers to develop cancer stem cell specific therapeutics. The present invention addresses this issue.

SUMMARY OF THE INVENTION

A set of markers for cancer stem cells are provided. The cells can be prospectively isolated or identified from primary tumor samples, and possess the unique properties of cancer stem cells in functional assays for tumor initiation, cancer stem cell self-renewal and differentiation. In addition, cancer stem cells can be used as a predictor for disease progression. The CSC have the phenotype of being positive for expression of CD271. The cells may be further characterized or selected for by expression of CD133, and expression of CD47. The CSC are negative for expression of certain well defined melanoma antigens, including MART-1, tyrosinase, HMB-45, and gp100.

In some embodiments of the invention, methods are provided for classification or clinical staging of melanoma according to the stem cells that are present, where greater numbers of stem cells are indicative of a more aggressive cancer phenotype. Staging is useful for prognosis and treatment. In some embodiments, a tumor sample is analyzed by flow cytometry, histochemistry, including immunohistochemistry, in situ hybridization, or the like, for the presence of cells that express CD271. The CSC may be further characterized as one or more of CD133$^+$, CD47$^+$, MART-1$^-$, tyrosinase$^-$, HMB-45$^-$, and gp100$^-$. The presence of such cells indicates the presence of CSC, and allows the definition of cancer stem cell domains in the primary tumor, as well as in metastases.

In another embodiment of the invention, compositions of isolated CSC having the phenotype described herein are provided. The cells are useful for experimental evaluation, and as a source of lineage and cell specific products, including mRNA species useful in identifying genes specifically expressed in these cells, and as targets for the discovery of factors or molecules that can affect them. CSC may be used, for example, in a method of screening a compound for an effect on the cells. This involves combining the compound with the cell population of the invention, and then determining any modulatory effect resulting from the compound. This may include examination of the cells for toxicity, metabolic change, or an effect on cell function. The phenotype of CSC described herein provides a means of predicting disease progression, relapse, and development of drug resistance.

In another embodiment of the invention, therapeutic compositions are provided of antigen specific agents that selectively bind to melanoma cancer stem cells, where the agent includes specificity for CD271. In some embodiments the therapeutic agent is a bispecific or multispecific reagent that recognizes a specificity selected from CD47 and CD271, and CD133 and CD271. Included are bispecific or multispecific antibodies, which are optionally conjugated to a detectable marker, chemotherapeutic agent are radionuclide for imaging or therapy.

BRIEF DESCRIPTION OF THE DRAWINGS

FIGS. 2A-2C. Isolation of melanoma tumor initiating cells (MTSC) expressing CD271P75(NGFR). a, Representative contour plot FACS gating sequence leading to purification of live, Lin−, CD271+ and C271− cells from Mel114 patient sample; CD271+ but not CD271− melanoma cells isolated from Mel1114 patient induce tumors upon intradermal injection in matrigel into Rag2−/− γc−/−(RG) mice at indicated cell doses after 28-32 weeks. b, Summary table of all injected cell doses and tumor frequency formation induced by CD271+, CD271− and bulk (Lin−) cell populations isolated directly from melanoma patients. Numbers indicate ratio of tumor incidence relative to the number of injections. c, Summary of CD271 P75(NGFR) limiting dilution analysis of the human melanoma tumor initiating cell for all patients; p values calculated as Student's t-Test (two-sample equal variance, one-tailed distribution).

DEFINITIONS

Figure 1:
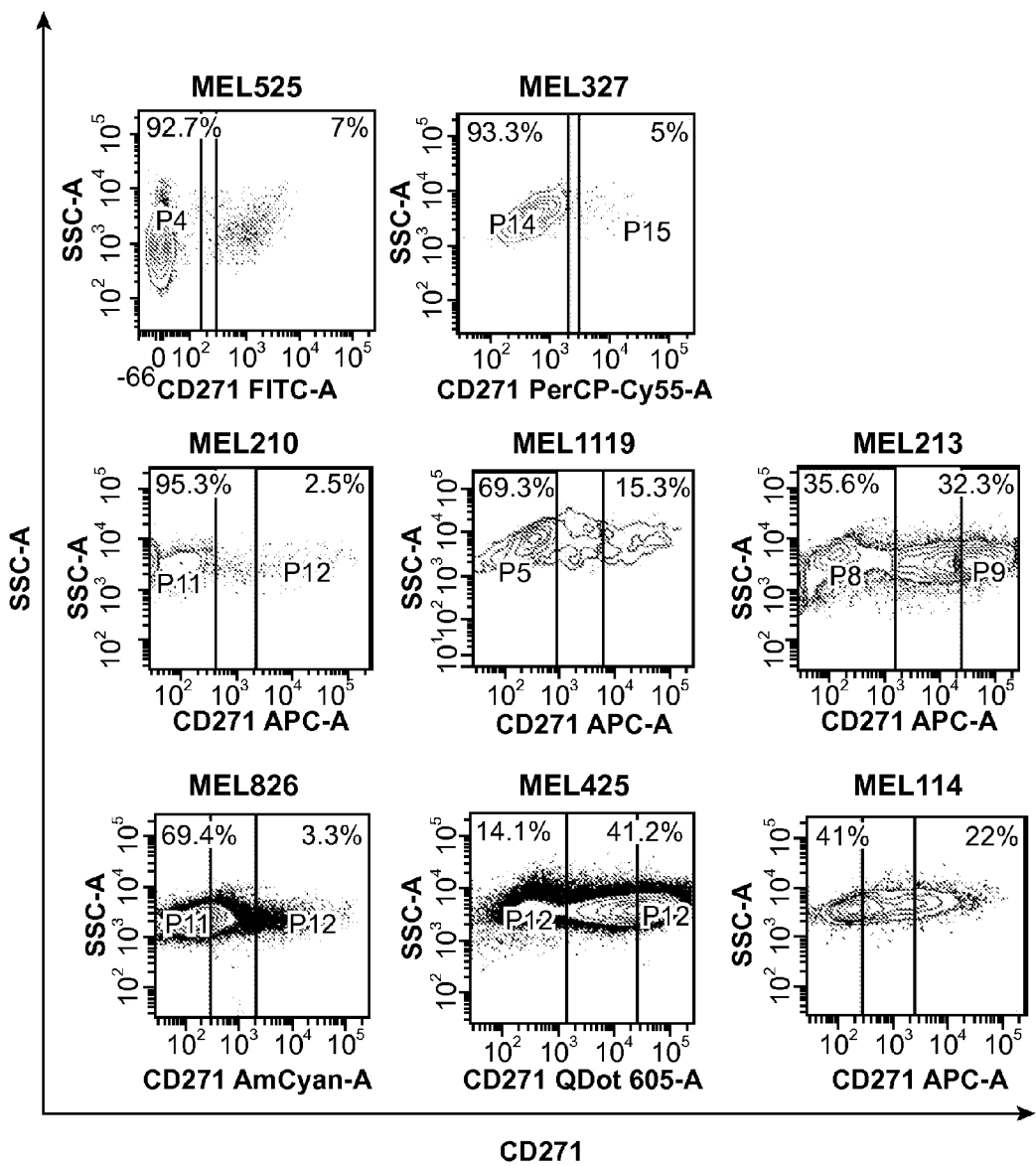
FIG. 1. Flow cytometric contour plots demonstrating the variable expression of CD271 in melanoma patients. Single cell suspensions were prepared from surgical samples and live, Lin− (CD45−) cells analyzed on BDFACSAria instrument.
Figure 2A:
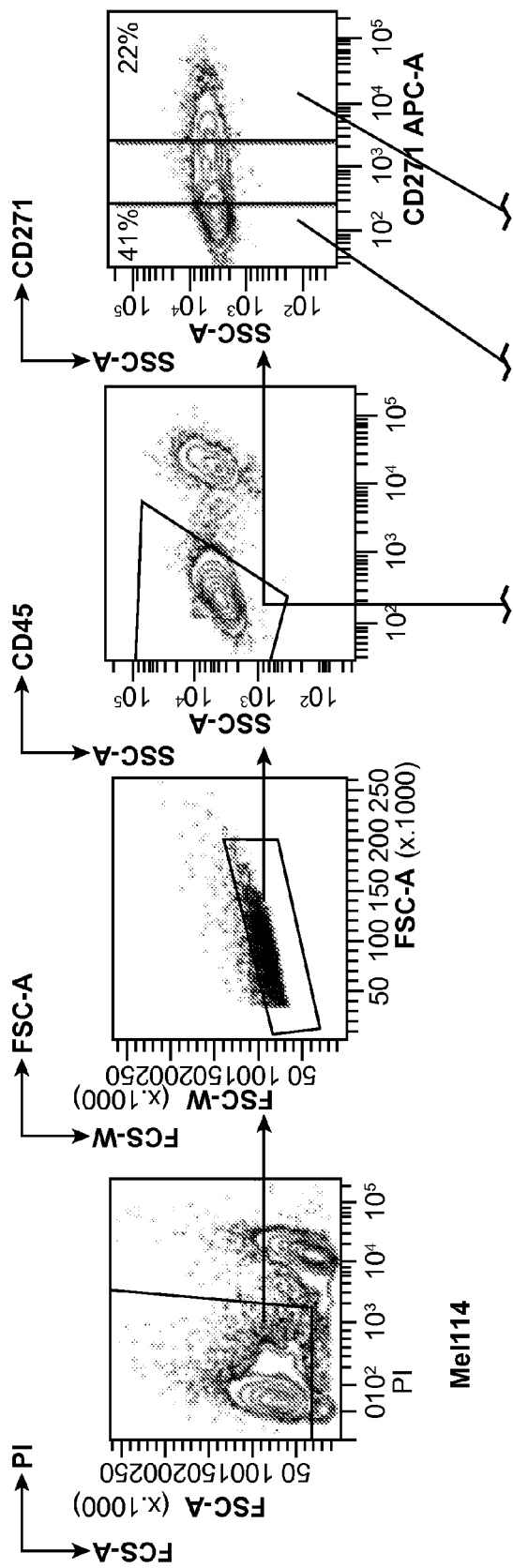
Figure 2A:
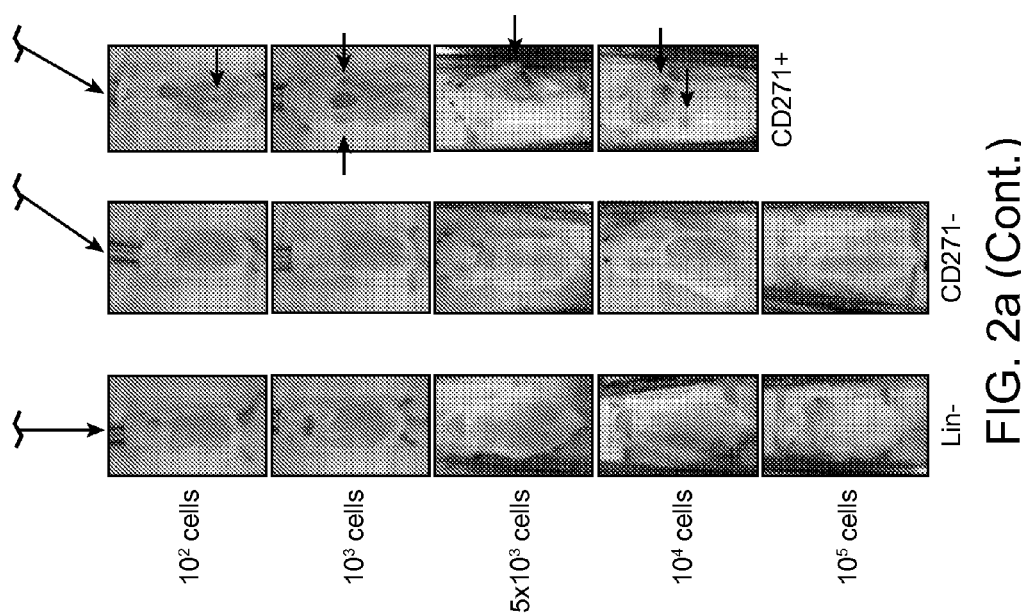
Figure 3A:
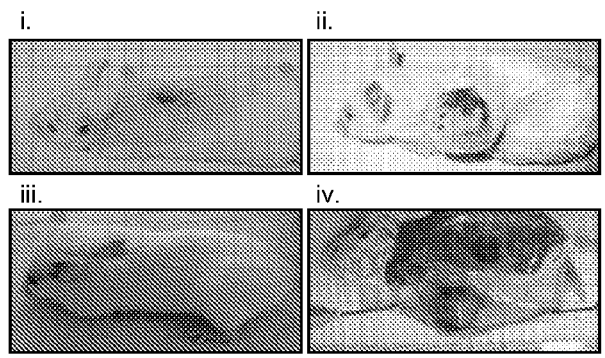
FIGS. 3A-3C. CD271+ melanoma tumor initiating cells induce tumors in humanized mouse models. a, Human skin graft in RG mice. (i) human skin graft appearance upon injection of 2×104 CD271− cells isolated from Mel43 primary skin Xenograft after 28 weeks; (ii-iii) melanoma tumor formation in human skin graft upon injection of 2×104 CD271+ cells isolated from Mel43 primary skin xenograft after 28 weeks; (iv) human skin graft appearance when no tumor cells were injected. b, Human skin graft RG mice. (i) human skin graft appearance upon injection of 2×104 CD271− cells isolated from Mel826, a primary dermal melanoma patient, after 16 weeks; (ii-iii) melanoma tumor formation in human skin graft upon injection of 6×103 CD271+ cells isolated from Mel826 after 16 weeks. c, Human bone graft in NOD/SCID Il2rg KO mice. (i) human bone graft appearance 20 weeks after injection of 103 CD271− cells isolated from Mel210, a melanoma patient with metastatic melanoma adjacent to the patella; (ii-iii) human bone graft appearance upon injection of 103 CD271+ cells isolated from Mel210 after 20 weeks.
Figure 3B:
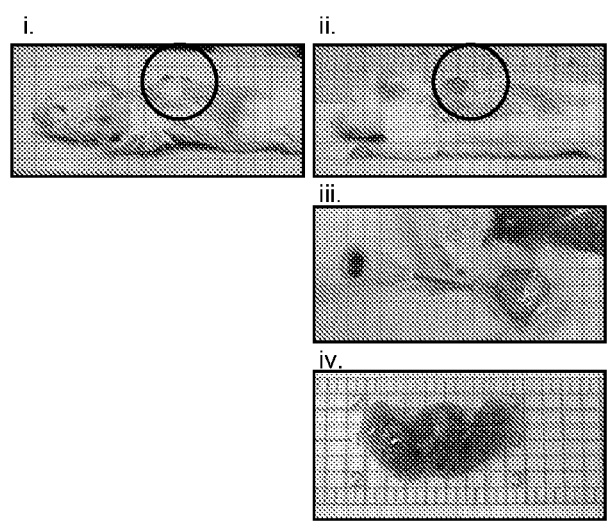
Figure 3C:
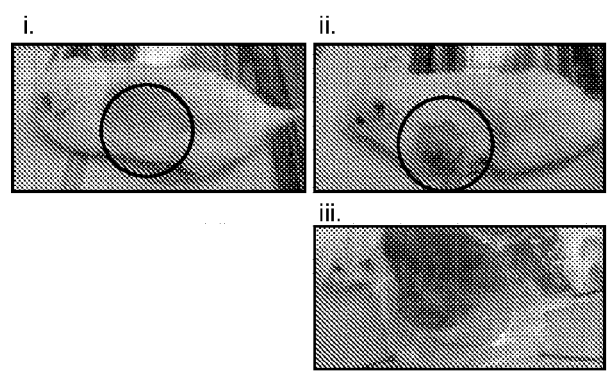
Figure 4A:
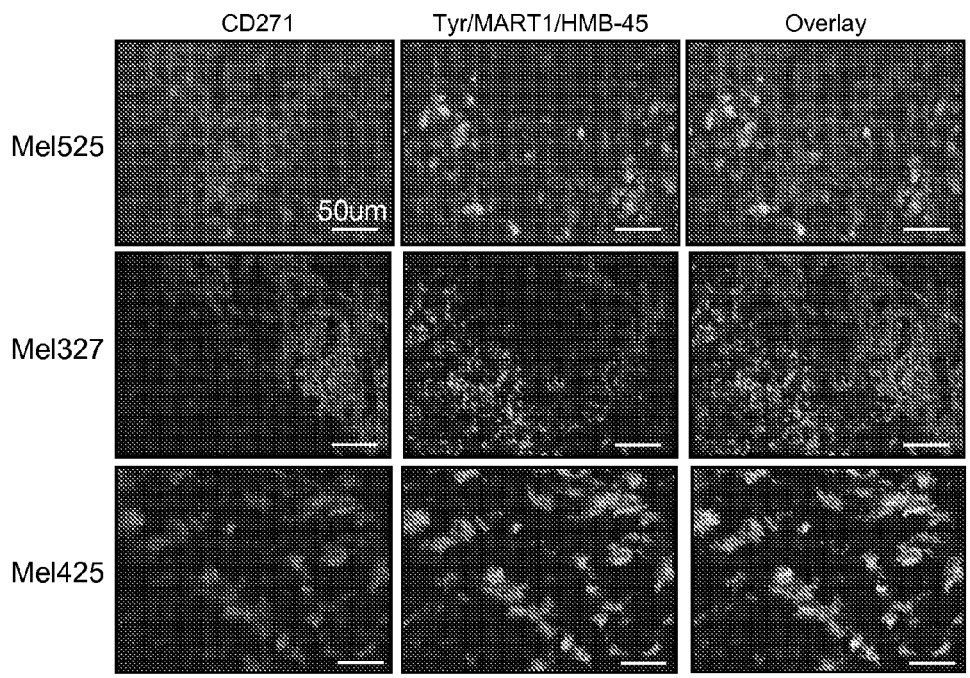
FIGS. 4A-4B. Immunofluorescent analysis of CD271, Tyr/MART1/HMB-45 and MAGE(C1-C2) expression in tissue sections of melanoma patients. a, Tissue sections of Mel525, Mel327 and Mel 425 melanoma specimens were stained with antibodies recognizing CD271and Tyr/MART1/HMB-45; b, CD271 and MAGE(C1-C2) followed by AlexaFluor 599/488 secondary antibodies. Nuclei were visualized with Hoechst 33342 Pictures were taken under 40× objective and scale bars are equal to 50 μm.
Figure 4B:
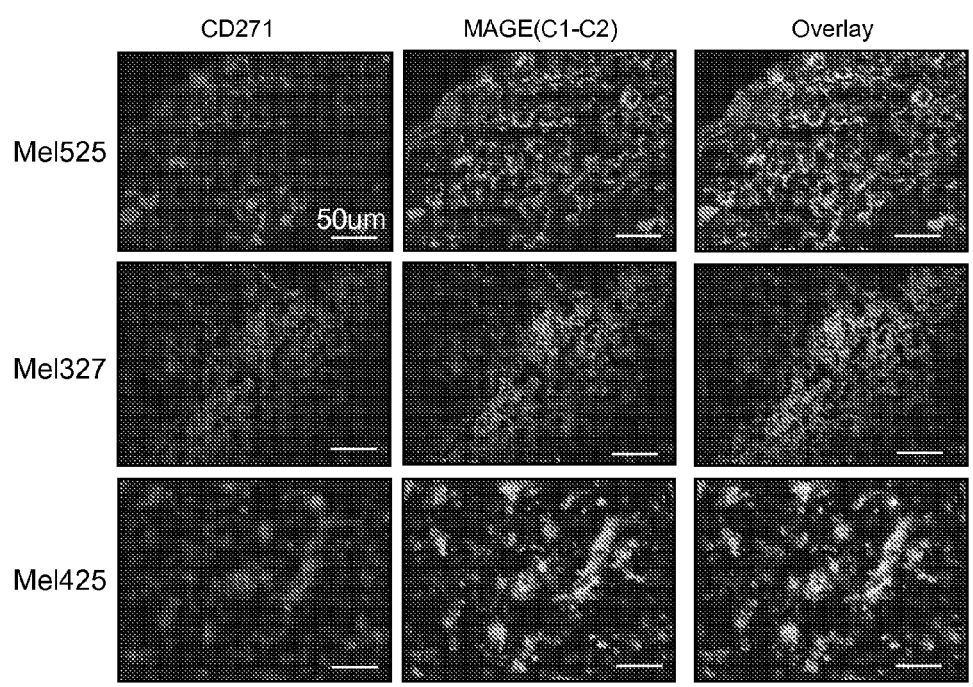

The term "stem cell" as used herein refers to a cell that (a) is capable of self-renewal; and (b) is a cell from which other types of cells can develop. A cancer stem cell is tumorigenic, i.e. it can initiate tumors in vivo. A cancer stem cell may also be metastatic, i.e. it can initiate tumors at a secondary site in the primary host, or in secondary hosts.

The term "progenitor cell" as used herein refers to a cell that (a) is not capable of self-renewal; and (b) is a cell from which other types of cells can develop.

The terms "cell proliferation" and "to proliferate" as used herein refer to the amplification of the cell by cell division.

The term "support" when applied to conditions under which cells are maintained, cultured, grown, proliferated, propagated or renewed, refers to conditions under which cells are capable of, respectively, being maintained, being cultured, growing, proliferating, propagating or renewing. Conditions can include cell culture media, concentrations of phosphate mimic, concentrations of stem and/or progenitor cell growth-modulating agent, or concentrations of growth factors. For example, a given cell culture media is said to "support" cell proliferation when a cell grown in said media is capable of proliferating.

As used herein, the term "isolated" when applied to a cell refers to a cell isolated from an animal, (e.g., a human, a rat, a mouse, etc.) and purified up to at least about 50%, such as 80%, 90% or more. Purity is measured by comparing the number of neural stem cells with the total number of cells. For example, an "80% pure" preparation of cancer stem cells means that 80% of the cells in the preparation are cancer stem cells.

CD271 (nerve growth factor receptor, NGFR) is a receptor with the ability to bind at low affinity not only NGF, but also other neurotrophins, including brain-derived neurotrophic factor, neurotrophin-3, and neurotrophin-4/5. It is a member of a large superfamily of tumor necrosis factor receptors having the overall structure of 4 extracellular ligand-binding, cysteine-rich repeats, or CRs, and signaling through association with, or disassociation from, cytoplasmic interactors. As a monomer, NGFR binds NGF with low affinity. Higher affinity binding is achieved by association with higher molecular mass, low-affinity neurotrophin receptors, namely the tropomyosin receptor kinases, TRKA (NTRK1; 191315), TRKB (NTRK2; 600456), and TRKC (NTRK3; 191316). The 3.8-kb NGFR mRNA encodes a 427-amino acid protein containing a 28-amino acid signal peptide, an extracellular domain containing four 40-amino acid repeats, each with 6 cysteine residues at conserved positions, followed by a serine/threonine-rich region, a single transmembrane domain, and a 155-amino acid cytoplasmic domain. The genetic sequence may be accessed at Genbank, NM_002507, as reported by Sehgal et al. (1988) Mol. Cell. Biol. 8 (8), 3160-3167.

"Bispecific antibody" and "bispecific antibodies," also known as bifunctional antibodies, refers to antibodies that recognize two different antigens by virtue of possessing at least one first antigen combining site specific for a first antigen or hapten, and at least one second antigen combining site specific for a second antigen or hapten. Multifunctional antibodies are also known in the art and may find use in the methods of the invention. Such antibodies can be produced by recombinant DNA methods or include, but are not limited to, antibodies produced chemically by methods known in the art. Bispecific antibodies include all antibodies or conjugates of antibodies, or polymeric forms of antibodies which are capable of recognizing two different antigens. Bispecific antibodies include antibodies that have been reduced and reformed so as to retain their bivalent characteristics and to antibodies that have been chemically coupled so that they can have several antigen recognition sites for each antigen.

The subject methods are useful for both prophylactic and therapeutic purposes. Thus, as used herein, the term "treating" is used to refer to both prevention of disease, and treatment of a pre-existing condition. The treatment of ongoing disease, to stabilize or improve the clinical symptoms of the patient, is a particularly important benefit provided by the present invention. Such treatment is desirably performed prior to loss of function in the affected tissues; consequently, the prophylactic therapeutic benefits provided by the invention are also important. For example, treatment of a cancer patient may be reduction of tumor size, elimination of malignant cells, prevention of metastasis, or the prevention of relapse in a patient who has been put into remission.

The terms "cell," and "cells," and "cell population," used interchangeably, intend one or more mammalian cells. The term includes progeny of a cell or cell population. Those skilled in the art will recognize that "cells" include progeny of a single cell, and the progeny can not necessarily be completely identical (in morphology or of total DNA complement) to the original parent cell due to natural, accidental, or deliberate mutation and/or change.

The term "substantially enriched" or "substantially isolated" as used herein, indicates that a cell population is at least about 20-fold, more preferably at least about 500-fold, and even more preferably at least about 5000-fold or more enriched from an original mixed cell population comprising the desired cell population.

A "subject" is a vertebrate, preferably a mammal, more preferably a human. Mammals include, but are not limited to, humans, farm animals, sport animals, and pets.

An "effective amount" is an amount sufficient to effect beneficial or desired clinical results. An effective amount can be administered in one or more administrations. For purposes of this invention, an effective amount of multivalent polypeptide is an amount that is sufficient to diagnose, palliate, ameliorate, stabilize, reverse, slow or delay the progression of the disease state.

DETAILED DESCRIPTION OF THE EMBODIMENTS

Before the present composition, methods, and isolation methodologies are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

Cancers are staged by analysis of the presence of cancer stem cells. Staging is useful for prognosis and treatment. In one embodiment of the invention, a sample from a patient is stained with reagents specific for CD271, and optionally for CD133, CD47, or melanoma associated antigens including MART-1, tyrosinase, HMB-45, and gp100. The analysis of staining patterns provides the relative distribution of CSC, which predicts the tumorigenicity of the tumor. In some embodiments, the sample is analyzed by flow cytometry or histochemistry for the presence of cells that express CD271, and optionally for CD133, CD47, or melanoma associated antigens including MART-1, tyrosinase, HMB-45, and gp100. In one embodiment, the patient sample is compared to a control, or a standard test value. In another embodiment, the patient sample is compared to a pre-cancer sample, or to one or more time points through the course of the disease.

Samples, including tissue sections, slides, etc. containing cancer tissue, are stained with reagents specific for markers that indicate the presence of cancer stem cells. Samples may be frozen, embedded, present in a tissue microarray, and the like. The reagents, e.g. antibodies, polynucleotide probes, etc. may be detectably labeled, or may be indirectly labeled in the staining procedure. The data provided herein demonstrate that the number and distribution of progenitor cells is diagnostic of the stage of the carcinoma.

The information thus derived is useful in prognosis and diagnosis, including susceptibility to acceleration of disease, status of a diseased state and response to changes in the environment, such as the passage of time, treatment with drugs or other modalities. The cells can also be classified as to their ability to respond to therapeutic agents and treatments, isolated for research purposes, screened for gene expression, and the like. The clinical samples can be further characterized by genetic analysis, proteomics, cell surface staining, or other means, in order to determine the presence of markers that are useful in classification. For example, genetic abnormalities can be causative of disease susceptibility or drug responsiveness, or can be linked to such phenotypes.

In another embodiment, an isolated multivalent reagent that specifically binds to CD271, and one or more of CD133 and CD47 surface markers is disclosed. In one aspect, the antibody is a bispecific antibody. In another aspect, the multivalent polypeptide is conjugated to a cytotoxic agent.

In another embodiment, a method for the treatment of cancer in a subject is disclosed, including administering to the subject, in an amount effective for the treatment, a pharmaceutical composition including (a) at least one reagent that (i) immunospecifically binds CD271 surface marker and optionally for CD133, CD47, or melanoma associated antigens including MART-1, tyrosinase, HMB-45, and gp100.and (ii) exerts a cytostatic or cytotoxic effect on a subpopulation of melanoma cancer stem cells; and (b) a pharmaceutically acceptable carrier.

In various embodiments, an agent that selectively binds CD 271 is an antibody comprising one or more of mouse IgG2a, mouse IgG2b, or human IgG1 constant region sequences, and which binds via the Fc region to the FcRII on macrophages and NK cells. The agent may be combined with an agent that selectively binds to or inhibits CD47, wherein to the agent that selectively binds CD271 engages FcRii on human macrophages and NK cells, and where the agents act synergistically to remove melanoma cancer stem cells. Mab anti CD271 and/or anti-CD 133 may be used as therapies along with anti-CD47 to enable phagocytosis and death of tumor stem cells. An anti-CD271 reagent may be a peptibody, or phage fusion protein, or recombined FcRII containing construct linked to a CD271 binding entity which along with CD 47 antibodies is used for therapy. Antibodies may be bivalent and monospecific, or bivalent and bispecific; [either to independent CD47 epitopes that don't cross-block in binding to the same CD47 molecule, but both combining sites bind to independent epitopes of CD47, as therapeutic agents acting alone or in combination with Mabs described in claims 16-21 except use soluble Sirp alpha molecules to block CD47

Conditions for Treatment

Cancer, as used herein, refers to hyperproliferative conditions. The term denotes malignant as well as non-malignant cell populations. Such disorders have an excess cell proliferation of one or more subsets of cells, which often appear to differ from the surrounding tissue both morphologically and genotypically. The excess cell proliferation can be determined by reference to the general population and/or by reference to a particular patient, e.g. at an earlier point in the patient's life. Hyperproliferative cell disorders can occur in different types of animals and in humans, and produce different physical manifestations depending upon the affected cells.

Malignant melanoma arises from melanocytes in a pigmented area, e.g. skin, mucous membranes, eyes, or CNS. About 60,000 new cases of melanoma occur yearly in the US, causing about 8400 deaths. Incidence has remained steady over the last 8 years. Melanomas occur mainly on the skin but also on the mucosa of the oral and genital regions and conjunctiva. Melanomas vary in size, shape, and color (usually pigmented) and in their propensity to invade and metastasize. Metastasis occurs via lymphatics and blood vessels. Local metastasis results in the formation of nearby satellite papules or nodules that may or may not be pigmented. Direct metastasis to skin or internal organs may occur, and occasionally, metastatic nodules or enlarged lymph nodes are discovered before the primary lesion is identified.

Risk factors include sun exposure, family and personal history, fair skin, increased numbers of melanocytic nevi, immunosuppression, occurrence of lentigo maligna, large congenital melanocytic nevus, and dysplastic nevus syndrome. Patients with a personal history of melanoma have an increased risk of additional melanomas. About 40 to 50% of melanomas develop from pigmented moles; almost all the rest arise from melanocytes in normal skin. Atypical moles (dysplastic nevi) may be precursors to melanoma. The very rare melanomas of childhood almost always arise from large pigmented moles (giant congenital nevi) present at birth.

There are 4 main types of melanoma. Lentigo maligna melanoma accounts for 5 to 15% of melanomas, and tends to arise in older patients. It arises from lentigo maligna. It appears on the face or other sun-exposed areas as an asymptomatic, flat, tan or brown, irregularly shaped macule or patch with darker brown or black spots scattered irregularly on its surface. In lentigo maligna, both normal and malignant melanocytes are confined to the epidermis. When malignant melanocytes invade the dermis, the lesion is called lentigo maligna melanoma, and the cancer may metastasize.

Superficial spreading melanoma accounts for the majority of melanomas. Typically asymptomatic, it occurs most commonly on women's legs and men's torsos. The lesion is usually a plaque with irregular, raised, indurated, tan or brown areas, which often have red, white, black, and blue spots or small, sometimes protuberant blue-black nodules. Small notchlike indentations of the margins may be noted, along with enlargement or color change. Histologically, atypical melanocytes characteristically invade the dermis and epidermis.

Nodular melanoma accounts for 10 to 15% of melanomas. It may occur anywhere on the body as a dark, protuberant papule or a plaque that varies from pearl to gray to black. Occasionally, a lesion contains little if any pigment or may look like a vascular tumor. Unless it ulcerates, nodular melanoma is asymptomatic, but patients usually seek advice because the lesion enlarges rapidly.

Acral-lentiginous melanoma: This type accounts for only 5 to 10% of melanomas, but it is the most common form of melanoma in blacks. It arises on palmar, plantar, and subungual skin and has a characteristic histologic picture similar to that of lentigo maligna melanoma.

The staging of melanoma is based on clinical and pathologic criteria and closely corresponds to the traditional tumor-node-metastasis (TNM) classification system. The staging system classifies melanomas based on local, regional, or distant disease. Stage I and II are localized primary melanoma; Stage III involves metastasis to regional lymph nodes; Stage IV is distant metastatic disease. Stage strongly correlates with survival. Melanomas may spread rapidly, causing death within months of its recognition, yet the 5-yr cure rate of early, very superficial lesions is nearly 100%. Thus, cure depends on early diagnosis and early treatment. Once melanoma has metastasized to the lymph nodes, 5-yr survival ranges from 25 to 70% depending on the degree of ulceration and number of nodes involved. Once melanoma has metastasized to distant sites, 5-yr survival is about 10%.

Conventional treatment, which may be combined with therapeutic methods of the present invention, include excision, imiquimod, and cryotherapy Metastatic disease is generally inoperable, but in certain cases, localized and regional metastases can be excised. Chemotherapy with dacarbazine or temazolamide and aldesleukin can be used for the treatment of metastatic melanoma. Adjuvant therapy with recombinant biologic response modifiers (particularly interferon-$\alpha$) to suppress clinically inapparent micrometastases may also be used for inoperable metastatic melanoma. Brain metastases may be treated with palliative radiation, but the response is poor.

Cancer Stem Cells

In one embodiment of the invention, a biologic sample from a cancer patient, e.g. a patient suffering from a melanoma as described above, is stained with reagents specific for CD271, and optionally for CD133, CD47, or melanoma associated antigens including MART-1, tyrosinase, HMB-45, and gp100. The analysis of staining patterns provides the relative distribution of cancer stem cells, which distribution predicts the tumorigenicity of the cancer, as well as the metastatic potential.

In one embodiment, the patient sample is compared to a control, or a standard test value. In another embodiment, the patient sample is compared to a pre-cancerous sample, or to one or more time points through the course of the disease.

The information thus derived is useful in prognosis and diagnosis, including susceptibility to acceleration of disease, status of a diseased state and response to changes in the environment, such as the passage of time, treatment with drugs or other modalities. The cells can also be classified as to their ability to respond to therapeutic agents and treatments, isolated for research purposes, screened for gene expression, and the like. The clinical samples can be further characterized by genetic analysis, proteomics, cell surface staining, or other means, in order to determine the presence of markers that are useful in classification. For example, genetic abnormalities can be causative of disease susceptibility or drug responsiveness, or can be linked to such phenotypes.

The presence of CSC in a patient sample can be indicative of the stage of a cancer. In addition, detection of CSC can be used to monitor response to therapy and to aid in prognosis. The presence of CSC can be determined by quantitating the cells having the phenotype of the CSC described herein.

In addition to cell surface phenotyping, it is useful to quantitate the cells in a sample that have a "stem cell" character. This can be determined by determining the ability of the cells to self-renew and proliferate in culture. Alternatively the cells can be tested for tumorigenicity in an animal model.

Clinical samples for use in the methods of the invention may be obtained from a variety of sources, particularly biopsy sample, although in some instances samples such as cerebrospinal fluid, blood and blood derivatives, and the like may be used. Such samples can be separated by centrifugation, elutriation, density gradient separation, apheresis, affinity selection, panning, FACS, centrifugation with Hypaque, etc. prior to analysis. Once a sample is obtained, it can be used directly, frozen, or maintained in appropriate culture medium for short periods of time. Various media can be employed to maintain cells. The samples may be obtained by any convenient procedure, such as the biopsy, or the like. Usually a sample will comprise at least about $10^2$ cells, more usually at least about $10^3$ cells, and preferable $10^4$, $10^5$ or more cells. Typically the samples will be from human patients, although animal models may find use, e.g. equine, bovine, porcine, canine, feline, rodent, e.g. mice, rats, hamster, primate, etc.

The labeled cells are quantitated as to the expression of cell surface markers. It is particularly convenient in a clinical setting to perform the immunoassay in a self-contained apparatus. A number of such methods are known in the art. The apparatus will generally employ a continuous flow-path of a suitable filter or membrane, having at least three regions, a fluid transport region, a sample region, and a measuring region. The sample region is prevented from fluid transfer contact with the other portions of the flow path prior to receiving the sample. After the sample region receives the sample, it is brought into fluid transfer relationship with the other regions, and the fluid transfer region contacted with fluid to permit a reagent solution to pass through the sample region and into the measuring region. The measuring region may have bound to it a conjugate of an enzyme with progenitor cell specific antibodies.

The comparison of a differential progenitor analysis obtained from a patient sample, and a reference differential progenitor analysis is accomplished by the use of suitable deduction protocols, AI systems, statistical comparisons, etc. A comparison with a reference differential progenitor analysis from normal cells, cells from similarly diseased tissue, and the like, can provide an indication of the disease staging. A database of reference differential progenitor analyses can be compiled. An analysis of particular interest tracks a patient, e.g. in the chronic and pre-leukemic stages of disease, such that acceleration of disease is observed at an early stage. The methods of the invention provide detection of acceleration prior to onset of clinical symptoms, and therefore allow early therapeutic intervention, e.g. initiation of chemotherapy, increase of chemotherapy dose, changing selection of chemotherapeutic drug, and the like.

Analysis by cell staining may use conventional methods, as known in the art. Techniques providing accurate enumeration include fluorescence activated cell sorters, which can have varying degrees of sophistication, such as multiple color channels, low angle and obtuse light scattering detecting channels, impedance channels, etc. The cells may be selected against dead cells by employing dyes associated with dead cells (e.g. propidium iodide).

The affinity reagents may be specific receptors or ligands for the cell surface molecules indicated above. In addition to antibody reagents, peptide-MHC antigen and T cell receptor pairs may be used; peptide ligands and receptor; effector and receptor molecules, and the like. Antibodies and T cell receptors may be monoclonal or polyclonal, and may be produced by transgenic animals, immunized animals, immortalized human or animal B-cells, cells transfected with DNA vectors encoding the antibody or T cell receptor, etc. The details of the preparation of antibodies and their suitability for use as specific binding members are well-known to those skilled in the art.

Of particular interest is the use of antibodies as affinity reagents. Conveniently, these antibodies are conjugated with a label for use in separation. Labels include magnetic beads, which allow for direct separation, biotin, which can be removed with avidin or streptavidin bound to a support, fluorochromes, which can be used with a fluorescence activated cell sorter, or the like, to allow for ease of separation of the particular cell type. Fluorochromes that find use include phycobiliproteins, e.g. phycoerythrin and allophycocyanins, fluorescein and Texas red. Frequently each antibody is labeled with a different fluorochrome, to permit independent sorting for each marker.

The antibodies are added to a suspension of cells, and incubated for a period of time sufficient to bind the available cell surface antigens. The incubation will usually be at least about 5 minutes and usually less than about 30 minutes. It is desirable to have a sufficient concentration of antibodies in the reaction mixture, such that the efficiency of the separation is not limited by lack of antibody. The appropriate concentration is determined by titration. The medium in which the cells are separated will be any medium that maintains the viability of the cells. A preferred medium is phosphate buffered saline containing from 0.1 to 0.5% BSA. Various media are commercially available and may be used according to the nature of the cells, including Dulbecco's Modified Eagle Medium (dMEM), Hank's Basic Salt Solution (HBSS), Dulbecco's phosphate buffered saline (dPBS), RPMI, Iscove's medium, PBS with 5 mM EDTA, etc., frequently supplemented with fetal calf serum, BSA, HSA, etc.

The labeled cells are then quantitated as to the expression of cell surface markers as previously described. It is particularly convenient in a clinical setting to perform the immunoassay in a self-contained apparatus. A number of such methods are known in the art. The apparatus will generally employ a continuous flow-path of a suitable filter or membrane, having at least three regions, a fluid transport region, a sample region, and a measuring region. The sample region is prevented from fluid transfer contact with the other portions of the flow path prior to receiving the sample. After the sample region receives the sample, it is brought into fluid transfer relationship with the other regions, and the fluid transfer region contacted with fluid to permit a reagent solution to pass through the sample region and into the measuring region. The measuring region may have bound to it a conjugate of an enzyme with progenitor cell specific antibodies.

CSC Compositions

The cells of interest may be separated from a complex mixture of cells by techniques that enrich for cells having the above described characteristics. For isolation of cells from tissue, an appropriate solution may be used for dispersion or suspension. Such solution will generally be a balanced salt solution, e.g. normal saline, PBS, Hank's balanced salt solution, etc., conveniently supplemented with fetal calf serum or other naturally occurring factors, in conjunction with an acceptable buffer at low concentration, generally from 5-25 mM. Convenient buffers include HEPES, phosphate buffers, lactate buffers, etc.

The separated cells may be collected in any appropriate medium that maintains the viability of the cells, usually having a cushion of serum at the bottom of the collection tube. Various media are commercially available and may be used according to the nature of the cells, including dMEM, HBSS, dPBS, RPMI, Iscove's medium, etc., frequently supplemented with fetal calf serum.

Compositions highly enriched for CSC are achieved in this manner, where the cells are $CD271^+$, and optionally selected to be $CD133^+$, $CD47^+$, and/or $MART-1^-$, $tyrosinase^-$, $HMB-45^-$, and $gp100^-$. The subject population may be at or about 50% or more of the cell composition, and preferably be at or about 75% or more of the cell composition, and may be 90% or more. The desired cells are identified by their surface phenotype, by the ability to self-renew, an essential property of stem cells. The enriched cell population may be used immediately, or may be frozen at liquid nitrogen temperatures and stored for long periods of time, being thawed and capable of being reused. The cells will usually be stored in 10% DMSO, 50% FCS, 40% RPMI 1640 medium. The population of cells enriched for CSC may be used in a variety of screening assays and cultures, as described below.

The enriched CSC population may be grown in vitro under various culture conditions. Culture medium may be liquid or semi-solid, e.g. containing agar, methylcellulose, etc. The cell population may be conveniently suspended in an appropriate nutrient medium, such as Iscove's modified DMEM or RPMI-1640, normally supplemented with fetal calf serum (about 5-10%), L-glutamine, a thiol, particularly 2-mercaptoethanol, and antibiotics, e.g. penicillin and streptomycin.

The culture may contain growth factors to which the cells are responsive. Growth factors, as defined herein, are molecules capable of promoting survival, growth and/or differentiation of cells, either in culture or in the intact tissue, through specific effects on a transmembrane receptor. Growth factors include polypeptides and non-polypeptide factors. A wide variety of growth factors may be used in culturing the cells, e.g. LIF, steel factor (c-kit ligand), EGF, insulin, IGF, NGF, etc. In addition to, or instead of growth factors, the subject cells may be grown in a co-culture with fibroblasts, stromal or other feeder layer cells.

The comparison of a differential progenitor analysis; or a CSC analysis obtained from a patient sample, and a reference analysis is accomplished by the use of suitable deduction protocols, artificial intelligence (AI) systems, statistical comparisons, etc. A comparison with a reference differential progenitor analysis from normal cells, cells from similarly diseased tissue, and the like, can provide an indication of the disease staging. A database of reference differential progenitor analyses can be compiled. An analysis of particular interest tracks a patient, e.g. in the chronic and pre-leukemic stages of disease, such that acceleration of disease is observed at an early stage. The methods of the invention provide detection of acceleration prior to onset of clinical symptoms, and therefore allow early therapeutic intervention, e.g. initiation of chemotherapy, increase of chemotherapy dose, changing selection of chemotherapeutic drug, and the like.

Screening Assays

CSC are useful for in vitro assays and screening to detect factors and chemotherapeutic agents that are active on cancer stem cells. Of particular interest are screening assays for agents that are active on human cells. A wide variety of assays may be used for this purpose, including immunoassays for protein binding; determination of cell growth, differentiation and functional activity; production of factors; and the like.

In screening assays for biologically active agents, anti-proliferative drugs; etc. the CSC composition, usually a culture comprising CSC, is contacted with the agent of interest, and the effect of the agent assessed by monitoring output parameters, such as expression of markers, cell viability, and the like. The cells may be freshly isolated, cultured, genetically altered as described above to provide a marker for activation of signaling pathways, and the like. The cells may be environmentally induced variants of clonal cultures: e.g. split into independent cultures and grown under distinct conditions, for example with or without drugs; in the presence or absence of cytokines or combinations thereof. The manner in which cells respond to an agent, particularly a pharmacologic agent, including the timing of responses, is an important reflection of the physiologic state of the cell.

Parameters are quantifiable components of cells, particularly components that can be accurately measured, desirably in a high throughput system. A parameter can be any cell component or cell product including cell surface determinant, receptor, protein or conformational or posttranslational modification thereof, lipid, carbohydrate, organic or inorganic molecule, nucleic acid, e.g. mRNA, DNA, etc. or a portion derived from such a cell component or combinations thereof. While most parameters will provide a quantitative readout, in some instances a semi-quantitative or qualitative result will be acceptable. Readouts may include a single determined value, or may include mean, median value or the variance, etc. Characteristically a range of parameter readout values will be obtained for each parameter from a multiplicity of the same assays. Variability is expected and a range of values for each of the set of test parameters will be obtained using standard statistical methods with a common statistical method used to provide single values.

Agents of interest for screening include known and unknown compounds that encompass numerous chemical classes, primarily organic molecules, which may include organometallic molecules, inorganic molecules, genetic sequences, etc. An important aspect of the invention is to evaluate candidate drugs, including toxicity testing; and the like.

In addition to complex biological agents candidate agents include organic molecules comprising functional groups necessary for structural interactions, particularly hydrogen bonding, and typically include at least an amine, carbonyl, hydroxyl or carboxyl group, frequently at least two of the functional chemical groups. The candidate agents often comprise cyclical carbon or heterocyclic structures and/or aromatic or polyaromatic structures substituted with one or more of the above functional groups. Candidate agents are also found among biomolecules, including peptides, polynucleotides, saccharides, fatty acids, steroids, purines, pyrimidines, derivatives, structural analogs or combinations thereof.

Included are pharmacologically active drugs, genetically active molecules, etc. Compounds of interest include chemotherapeutic agents, hormones or hormone antagonists, etc. Exemplary of pharmaceutical agents suitable for this invention are those described in, "The Pharmacological Basis of Therapeutics," Goodman and Gilman, McGraw-Hill, New York, N.Y., (1996), Ninth edition, under the sections: Water, Salts and Ions; Drugs Affecting Renal Function and Electrolyte Metabolism; Drugs Affecting Gastrointestinal Function; Chemotherapy of Microbial Diseases; Chemotherapy of Neoplastic Diseases; Drugs Acting on Blood-Forming organs; Hormones and Hormone Antagonists; Vitamins, Dermatology; and Toxicology, all incorporated herein by reference. Also included are toxins, and biological and chemical warfare agents, for example see Somani, S. M. (Ed.), "Chemical Warfare Agents," Academic Press, New York, 1992).

Test compounds include all of the classes of molecules described above, and may further comprise samples of unknown content. Of interest are complex mixtures of naturally occurring compounds derived from natural sources such as plants. While many samples will comprise compounds in solution, solid samples that can be dissolved in a suitable solvent may also be assayed. Samples of interest include environmental samples, e.g. ground water, sea water, mining waste, etc.; biological samples, e.g. lysates prepared from crops, tissue samples, etc.; manufacturing samples, e.g. time course during preparation of pharmaceuticals; as well as libraries of compounds prepared for analysis; and the like. Samples of interest include compounds being assessed for potential therapeutic value, i.e. drug candidates.

The term samples also includes the fluids described above to which additional components have been added, for example components that affect the ionic strength, pH, total protein concentration, etc. In addition, the samples may be treated to achieve at least partial fractionation or concentration. Biological samples may be stored if care is taken to reduce degradation of the compound, e.g. under nitrogen, frozen, or a combination thereof. The volume of sample used is sufficient to allow for measurable detection, usually from about 0.1 µl to 1 ml of a biological sample is sufficient.

Compounds, including candidate agents, are obtained from a wide variety of sources including libraries of synthetic or natural compounds. For example, numerous means are available for random and directed synthesis of a wide variety of organic compounds, including biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Agents are screened for biological activity by adding the agent to at least one and usually a plurality of cell samples, usually in conjunction with cells lacking the agent. The change in parameters in response to the agent is measured, and the result evaluated by comparison to reference cultures, e.g. in the presence and absence of the agent, obtained with other agents, etc.

The agents are conveniently added in solution, or readily soluble form, to the medium of cells in culture. The agents may be added in a flow-through system, as a stream, intermittent or continuous, or alternatively, adding a bolus of the compound, singly or incrementally, to an otherwise static solution. In a flow-through system, two fluids are used, where one is a physiologically neutral solution, and the other is the same solution with the test compound added. The first fluid is passed over the cells, followed by the second. In a single solution method, a bolus of the test compound is added to the volume of medium surrounding the cells. The overall concentrations of the components of the culture medium should not change significantly with the addition of the bolus, or between the two solutions in a flow through method.

Preferred agent formulations do not include additional components, such as preservatives, that may have a significant effect on the overall formulation. Thus preferred formulations consist essentially of a biologically active compound and a physiologically acceptable carrier, e.g. water, ethanol, DMSO, etc. However, if a compound is liquid without a solvent, the formulation may consist essentially of the compound itself.

A plurality of assays may be run in parallel with different agent concentrations to obtain a differential response to the various concentrations. As known in the art, determining the effective concentration of an agent typically uses a range of concentrations resulting from 1:10, or other log scale, dilutions. The concentrations may be further refined with a second series of dilutions, if necessary. Typically, one of these concentrations serves as a negative control, i.e. at zero concentration or below the level of detection of the agent or at or below the concentration of agent that does not give a detectable change in the phenotype.

Various methods can be utilized for quantifying the presence of the selected markers. For measuring the amount of a molecule that is present, a convenient method is to label a molecule with a detectable moiety, which may be fluorescent, luminescent, radioactive, enzymatically active, etc., particularly a molecule specific for binding to the parameter with high affinity. Fluorescent moieties are readily available for labeling virtually any biomolecule, structure, or cell type. Immunofluorescent moieties can be directed to bind not only to specific proteins but also specific conformations, cleavage products, or site modifications like phosphorylation. Individual peptides and proteins can be engineered to autofluoresce, e.g. by expressing them as green fluorescent protein chimeras inside cells. (for a review see Jones et al. (1999) Trends Biotechnol. 17(12):477-81). Thus, antibodies can be genetically modified to provide a fluorescent dye as part of their structure. Depending upon the label chosen, parameters may be measured using other than fluorescent labels, using such immunoassay techniques as radioimmunoassay (RIA) or enzyme linked immunosorbance assay (ELISA), homogeneous enzyme immunoassays, and related non-enzymatic techniques. The quantitation of nucleic acids, especially messenger RNAs, is also of interest as a parameter. These can be measured by hybridization techniques that depend on the sequence of nucleic acid nucleotides. Techniques include polymerase chain reaction methods as well as gene array techniques. See Current Protocols in Molecular Biology, Ausubel et al., eds, John Wiley & Sons, New York, N.Y., 2000; Freeman et al. (1999) Biotechniques 26(1):112-225; Kawamoto et al. (1999) Genome Res 9(12):1305-12; and Chen et al. (1998) Genomics 51(3):313-24, for examples.

Kits may be provided, where the kit will comprise a staining reagents that are sufficient to differentially identify the NCSC. A marker combination of interest may include *** and CD271. The staining reagents are preferably antibodies, and may be detectably labeled. Kits may also include tubes, buffers, etc., and instructions for use.

Therapeutic Agents

Generally, suitable therapeutic agents for practicing the methods of the present invention immunospecifically bind CD271, and optionally bind CD133 or CD47. The invention provides methods for reducing growth of melanoma cancer cells, particularly melanoma cancer stem cells, through the introduction of a CD271 blocking agent, e.g. an anti-CD271 antibody, small molecule, etc., which may be performed in combination with a second agent that specifically binds to a second CSC marker, or which is a conventional chemotherapeutic agent.

"Reducing growth of cancer cells" includes, but is not limited to, reducing proliferation of cancer cells, and reducing the incidence of a non-cancerous cell becoming a cancerous cell. Whether a reduction in cancer cell growth has been achieved can be readily determined using any known assay, including, but not limited to, [$^3$H]-thymidine incorporation; counting cell number over a period of time; detecting and/or measuring a marker associated with melanoma, etc.

Whether a substance, or a specific amount of the substance, is effective in treating cancer can be assessed using any of a variety of known diagnostic assays for cancer, including, but not limited to biopsy, contrast radiographic studies, CAT scan, and detection of a tumor marker associated with cancer in the blood of the individual. The substance can be administered systemically or locally, usually systemically.

In some embodiments, the invention provides a method of delivering a drug to a cancer cell, comprising administering a drug-antibody complex to a subject, wherein the antibody is specific for a cancer-associated polypeptide, and the drug is one that reduces cancer cell growth, a variety of which are known in the art. Targeting can be accomplished by coupling (e.g., linking, directly or via a linker molecule, either covalently or non-covalently, so as to form a drug-antibody complex) a drug to an antibody specific for a cancer-associated polypeptide. Methods of coupling a drug to an antibody are well known in the art and need not be elaborated upon herein.

Antibodies suitable for practicing the methods of the invention are preferably monoclonal and multivalent, and may be human, humanized or chimeric antibodies, comprising single chain antibodies, Fab fragments, F(ab') fragments, fragments produced by a Fab expression library, and/or binding fragments of any of the above. The term "antibody," as used herein, refers to immunoglobulin molecules and immunologically active portions of immunoglobulin molecules, i.e., molecules that contain at least two antigen binding sites that immunospecifically bind CD3 and CD11b. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule. In certain embodiments of the invention, the antibodies are human antigen-binding antibody fragments of the present invention and include, but are not limited to, Fab, Fab' and F(ab')$_2$, Fd, single-chain Fvs (scFv), single-chain antibodies, disulfide-linked Fvs (sdFv) and fragments comprising either a $V_L$ or $V_H$ domain. Antigen-binding antibody fragments, including single-chain antibodies, may comprise the variable region(s) alone or in combination with the entirety or a portion of the following: hinge region, $CH_1$, $CH_2$, $CH_3$ and CL domains. Also included in the invention are antigen-binding fragments comprising any combination of variable region(s) with a hinge region, $CH_1$, $CH_2$, $CH_3$ and CL domains. Preferably, the antibodies are human, murine (e.g., mouse and rat), donkey, sheep, rabbit, goat, guinea pig, camelid, horse, or chicken. As used herein, "human" antibodies include antibodies having the amino acid sequence of a human immunoglobulin and include antibodies isolated from human immunoglobulin libraries, from human B cells, or from animals transgenic for one or more human immunoglobulins.

The antibodies suitable for practicing the methods of the present invention may be bispecific, trispecific or of greater multispecificity. Further, the antibodies of the present invention may have low risk of toxicity against granulocyte (neutrophil), NK cells, and CD$^+$ cells as bystander cells.

Methods for making bispecific antibodies are known in the art. Traditional production of full length bispecific antibodies is based on the coexpression of two immunoglobulin heavy chain-light chain pairs, where the two chains have different specificities (Millstein et al., Nature, 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al, EMBO J., 10:3655-3659 (1991).

According to another approach described in WO96/27011, the interface between a pair of antibody molecules can be engineered to maximize the percentage of heterodimers which are recovered from recombinant cell culture. Such interfaces may comprise at least a part of the $CH_3$ domain of an antibody constant domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676, 980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., Science, 229:81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Various techniques for making and isolating bispecific antibody fragments directly from recombinant cell culture have also been described. For example, bispecific antibodies have been produced using leucine zippers. Kostelny et al., J. Immunol, 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA, 90:6444-6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., J. Immunol., 152:5368 (1994). Alternatively, the antibodies can be "linear antibodies" as described in Zapata et al. Protein Eng. 8(10): 1057-1062 (1995). Briefly, these antibodies comprise a pair of tandem Fd segments ($V_H$-$C_{H1}$-$V_H$-$C_H$1) which form a pair of antigen binding regions. Linear antibodies can be bispecific or monospecific.

Multivalent antibodies may be specific for different epitopes of CD271, CD47 and CD133, including, for example, that the multivalent antibodies may bind to one or more of the epitopes present on CD271. Multivalent antibodies, including bispecific and trispecific antibodies, useful for practicing the present invention are antibodies that immunospecifically bind to both CD271 and CD47 or CD133, and may bind one of more additional cancer surface receptors or receptor complexes.

Antibodies useful in the present methods may be described or specified in terms of the particular CDRs they comprise. The invention encompasses the use of an antibody or derivative thereof comprising a heavy or light chain variable domain, said variable domain comprising (a) a set of three CDRs, and (b) a set of four framework regions, and in which said antibody or derivative thereof immunospecifically binds CD271.

Within the context of the present invention, antibodies are understood to include monoclonal antibodies and polyclonal antibodies, antibody fragments (e.g., Fab and F(ab')$_2$), chimeric antibodies bifunctional or bispecific antibodies and tetrameric antibody complexes. Antibodies are understood to be reactive against a selected antigen on the surface of a T cell if they bind with an appropriate affinity (association constant), e.g. greater than or equal to $10^7 M^{-1}$. Additionally, antibodies that may be used in the methods of the present invention may also be described or specified in terms of their binding affinities include those with a dissociation constant or Kd less than $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, $10^{-5}$ M, $5 \times 10^{-6}$ M, $10^{-6}$ M, $5 \times 10^{-7}$ M, $10^{-7}$ M, $5 \times 10^{-8}$ M, $10^{-8}$ M, $5 \times 10^{-9}$ M, $10^{-9}$ M, $5 \times 10^{-10}$ M, $10^{-9}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, $10^{-15}$ M.

Antibodies can be fragmented using conventional techniques and the fragments screened for utility in the same manner as described above for the whole antibodies. For example, F(ab')$_2$ fragments can be generated by treating antibody with pepsin. The resulting F(ab')$_2$ fragment can be treated to reduce disulfide bridges to produce Fab' fragments The invention also contemplates chimeric antibody derivatives, i.e., antibody molecules that combine a non-human animal variable region and a human constant region. Chimeric antibody molecules can include, for example, the antigen binding domain from an antibody of a mouse, rat, or other species, with human constant regions. A variety of approaches for making chimeric antibodies have been described and can be used to make chimeric antibodies containing the immunoglobulin variable region which recognizes the selected antigens on the surface of differentiated cells or tumor cells. See, for example, Morrison et al., 1985; Proc. Natl. Acad. Sci. U.S.A. 81,6851; Takeda et al., 1985, Nature 314:452; Cabilly et al., U.S. Pat. No. 4,816,567; Boss et al., U.S. Pat. No. 4,816,397; Tanaguchi et al., European Patent Publication EP171496; European Patent Publication 0173494, United Kingdom patent GB 2177096B.

Chemical conjugation is based on the use of homo- and heterobifunctional reagents with E-amino groups or hinge region thiol groups. Homobifunctional reagents such as 5,5'-Dithiobis(2-nitrobenzoic acid) (DNTB) generate disulfide bonds between the two Fabs, and 0-phenylenedimaleimide (O-PDM) generate thioether bonds between the two Fabs (Brenner et al., 1985, Glennie et al., 1987). Heterobifunctional reagents such as N-succinimidyl-3-(2-pyridylditio) propionate (SPDP) combine exposed amino groups of antibodies and Fab fragments, regardless of class or isotype (Van Dijk et al., 1989).

The antibodies of the invention, i.e., antibodies that are useful for treating cancers, as well as other cancer comprising cancer stem cells expressing CD271, include derivatives that are modified, i.e., by the covalent attachment of any type of molecule to the antibody such that covalent attachment does not prevent the antibody from binding to CD271. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

The antibodies may be generated by any suitable method known in the art. Polyclonal antibodies can be produced by various procedures well known in the art. For example, CD271 can be administered to various host animals including, but not limited to, rabbits, mice, rats, etc. to induce the production of sera containing polyclonal antibodies specific for the protein. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and corynebacteriumparvum. Such adjuvants are also well known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed., 1988); Hammer-ling, et al., in: Monoclonal Antibodies and T-Cell Hybrido-mas 563-681 (Elsevier, N.Y., 1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced. Methods for producing and screening for specific antibodies using hybridoma technology are routine and well known in the art.

Antibody fragments which recognize specific epitopes may be generated by known techniques. For example, Fab and F(ab')$_2$ fragments of the invention may be produced by proteolytic cleavage of immunoglobulin molecules, using enzymes such as papain (to produce Fab fragments) or pepsin (to produce F(ab').sub.2 fragments). F(ab')$_2$ fragments contain the variable region, the light chain constant region and the $CH_1$ domain of the heavy chain.

For example, antibodies useful in the methods of the present invention can also be generated using various phage display methods known in the art.

Completely human antibodies are particularly desirable for the therapeutic treatment of human patients. Human antibodies can be made by a variety of methods known in the art including phage display methods described above using antibody libraries derived from human immunoglobulin sequences. See also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741.

Pharmaceutical compositions can include, depending on the formulation desired, pharmaceutically-acceptable, non-toxic carriers of diluents, which are defined as vehicles commonly used to formulate pharmaceutical compositions for animal or human administration. The diluent is selected so as not to affect the biological activity of the combination. Examples of such diluents are distilled water, buffered water, physiological saline, PBS, Ringer's solution, dextrose solution, and Hank's solution. In addition, the pharmaceutical composition or formulation can include other carriers, adjuvants, or non-toxic, nontherapeutic, nonimmunogenic stabilizers, excipients and the like. The compositions can also include additional substances to approximate physiological conditions, such as pH adjusting and buffering agents, toxicity adjusting agents, wetting agents and detergents.

The composition can also include any of a variety of stabilizing agents, such as an antioxidant for example. When the pharmaceutical composition includes a polypeptide, the polypeptide can be complexed with various well-known compounds that enhance the in vivo stability of the polypeptide, or otherwise enhance its pharmacological properties (e.g., increase the half-life of the polypeptide, reduce its toxicity, enhance solubility or uptake). Examples of such modifications or complexing agents include sulfate, gluconate, citrate and phosphate. The polypeptides of a composition can also be complexed with molecules that enhance their in vivo attributes. Such molecules include, for example, carbohydrates, polyamines, amino acids, other peptides, ions (e.g., sodium, potassium, calcium, magnesium, manganese), and lipids.

Further guidance regarding formulations that are suitable for various types of administration can be found in Remington's Pharmaceutical Sciences, Mace Publishing Company, Philadelphia, Pa., 17th ed. (1985). For a brief review of methods for drug delivery, see, Langer, Science 249:1527-1533 (1990).

The pharmaceutical compositions can be administered for prophylactic and/or therapeutic treatments. Toxicity and therapeutic efficacy of the active ingredient can be determined according to standard pharmaceutical procedures in cell cultures and/or experimental animals, including, for example, determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$ Compounds that exhibit large therapeutic indices are preferred.

The data obtained from cell culture and/or animal studies can be used in formulating a range of dosages for humans. The dosage of the active ingredient typically lines within a range of circulating concentrations that include the $ED_{50}$ with low toxicity. The dosage can vary within this range depending upon the dosage form employed and the route of administration utilized.

The pharmaceutical compositions described herein can be administered in a variety of different ways. Examples include administering a composition containing a pharmaceutically acceptable carrier via oral, intranasal, rectal, topical, intraperitoneal, intravenous, intramuscular, subcutaneous, subdermal, transdermal, intrathecal, and intracranial methods.

For oral administration, the active ingredient can be administered in solid dosage forms, such as capsules, tablets, and powders, or in liquid dosage forms, such as elixirs, syrups, and suspensions. The active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate. Examples of additional inactive ingredients that may be added to provide desirable color, taste, stability, buffering capacity, dispersion or other known desirable features are red iron oxide, silica gel, sodium lauryl sulfate, titanium dioxide, and edible white ink. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

The active ingredient, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions.

The compositions of the invention may be administered using any medically appropriate procedure, e.g., intravascular (intravenous, intraarterial, intracapillary) administration, injection into the cerebrospinal fluid, intracavity or direct injection in the tumor. Intrathecal administration maybe carried out through the use of an Ommaya reservoir, in accordance with known techniques. (F. Balis et al., Am J. Pediatr. Hematol. Oncol. 11,74,76 (1989). For the imaging compositions of the invention, administration via intravascular injection is preferred for pre-operative visualization of the tumor. Post-operative visualization or visualization concurrent with an operation may be through intrathecal or intracavity administration, as through an Ommaya reservoir, or also by intravascular administration.

Where the therapeutic agents are administered in combination with treatment of brain tumors, one method for administration of the therapeutic compositions of the invention is by deposition into or near the tumor by any suitable technique, such as by direct injection (aided by stereotaxic positioning of an injection syringe, if necessary) or by placing the tip of an Ommaya reservoir into a cavity, or cyst, for administration. Alternatively, a convection-enhanced delivery catheter may be implanted directly into the tumor mass, into a natural or surgically created cyst, or into the normal brain mass. Such convection-enhanced pharmaceutical composition delivery devices greatly improve the diffusion of the composition throughout the brain mass. The implanted catheters of these delivery devices utilize highflow microinfusion (with flow rates in the range of about 0.5 to 15.0 .mu.l/minute), rather than diffusive flow, to deliver the therapeutic composition to the brain and/or tumor mass. Such devices are described in U.S. Pat. No. 5,720,720, incorporated fully herein by reference.

The compositions can be administered to the subject in a series of more than one administration. For therapeutic compositions, regular periodic administration will sometimes be required, or may be desirable. Therapeutic regimens will vary with the agent, e.g. daily or semi-daily basis; administered for more defined time courses, e.g. one, two three or more days, one or more weeks, one or more months, etc., taken daily, semi-daily, semiweekly, weekly, etc.

Formulations may be optimized for retention and stabilization in the brain. When the agent is administered into the cranial compartment, it is desirable for the agent to be retained in the compartment, and not to diffuse or otherwise cross the blood brain barrier. Stabilization techniques include cross-linking, multimerizing, or linking to groups such as polyethylene glycol, polyacrylamide, neutral protein carriers, etc. in order to achieve an increase in molecular weight.

Other strategies for increasing retention include the entrapment of the agent in a biodegradable or bioerodible implant. The rate of release of the therapeutically active agent is controlled by the rate of transport through the polymeric matrix, and the biodegradation of the implant. The transport of drug through the polymer barrier will also be affected by compound solubility, polymer hydrophilicity, extent of polymer crosslinking, expansion of the polymer upon water absorption so as to make the polymer barrier more permeable to the drug, geometry of the implant, and the like. The implants are of dimensions commensurate with the size and shape of the region selected as the site of implantation. Implants may be particles, sheets, patches, plaques, fibers, microcapsules and the like and may be of any size or shape compatible with the selected site of insertion.

The implants may be monolithic, i.e. having the active agent homogenously distributed through the polymeric matrix, or encapsulated, where a reservoir of active agent is encapsulated by the polymeric matrix. The selection of the polymeric composition to be employed will vary with the site of administration, the desired period of treatment, patient tolerance, the nature of the disease to be treated and the like. Characteristics of the polymers will include biodegradability at the site of implantation, compatibility with the agent of interest, ease of encapsulation, a half-life in the physiological environment.

Biodegradable polymeric compositions which may be employed may be organic esters or ethers, which when degraded result in physiologically acceptable degradation products, including the monomers. Anhydrides, amides, orthoesters or the like, by themselves or in combination with other monomers, may find use. The polymers will be condensation polymers. The polymers may be cross-linked or non-cross-linked. Of particular interest are polymers of hydroxy-aliphatic carboxylic acids, either homo- or copolymers, and polysaccharides. Included among the polyesters of interest are polymers of D-lactic acid, L-lactic acid, racemic lactic acid, glycolic acid, polycaprolactone, and combinations thereof. By employing the L-lactate or D-lactate, a slowly biodegrading polymer is achieved, while degradation is substantially enhanced with the racemate. Copolymers of glycolic and lactic acid are of particular interest, where the rate of biodegradation is controlled by the ratio of glycolic to lactic acid. The most rapidly degraded copolymer has roughly equal amounts of glycolic and lactic acid, where either homopolymer is more resistant to degradation. The ratio of glycolic acid to lactic acid will also affect the brittleness of in the implant, where a more flexible implant is desirable for larger geometries. Among the polysaccharides of interest are calcium alginate, and functionalized celluloses, particularly carboxymethylcellulose esters characterized by being water insoluble, a molecular weight of about 5 kD to 500 kD, etc. Biodegradable hydrogels may also be employed in the implants of the subject invention. Hydrogels are typically a copolymer material, characterized by the ability to imbibe a liquid. Exemplary biodegradable hydrogels which may be employed are described in Heller in: Hydrogels in Medicine and Pharmacy, N. A. Peppes ed., Vol. III, CRC Press, Boca Raton, Fla., 1987, pp 137-149.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration.

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention, which will be limited only by the appended claims.

As used herein the singular forms "a", "and", and "the" include plural referents unless the context clearly dictates otherwise. Thus, for example, reference to "a cell" includes a plurality of such cells and reference to "the culture" includes reference to one or more cultures and equivalents thereof known to those skilled in the art, and so forth. All technical and scientific terms used herein have the same meaning as commonly understood to one of ordinary skill in the art to which this invention belongs unless clearly indicated otherwise.

EXPERIMENTAL

Example 1

The question whether tumorigenic cancer initiating cells [cancer stem cells{CSC}] exist in human melanomas has arisen recently. Here we show that in melanomas cancer stem cells can be isolated prospectively as a highly enriched CD271+ CSC population using the improved methods of tumor initiation, where the tumors sampled in the present study were taken from primary sites rather than from metastatic sites or grafts passaged in NOG mice. At all stages tested the CD271+ subset of cells in the tumor were the only tumorigenic fraction in melanomas tested; and CD271+ cells contain the metastasis initiation tumor population. The expression level of CD271 is a factor for increased risk of poor outcome in melanoma patients. The melanoma antigens MART-1, Tyr, and HMB-45 are restricted to the CD271$^-$ fraction. MAGE is expressed in some, but not all CD271$^{30}$ melanoma cells.

Cancers derive by clonal progression to appear as abnormal growths which can be at diagnosis at a stage ranging from just beyond benign to highly aggressive and metastatic. At early stages the self-renewing minority population can differentiate nonmalignant progeny, and at later stages the self-renewing cancer stem cell population may become the dominant population in a tumor. We began the search for the tumorigenic subset of patient melanomas separating the cells with Mabs to CD271, using established methods of FACS separations that yield cells with high viability, implanting the tumor cells in a matrigel vehicle, and using T, B, and NK deficient Rag2$^{-/-}$ γc$^{-/-}$ mice as recipients.

Melanoma samples that included primary skin lesions, as well as visceral metastases, were used to profile expression of candidate stem cell markers. Hours after surgical resection fresh tumor samples from melanoma patients were mechanically and enzymatically dissociated to obtain mixture containing single cells. The resulting cell suspension was subjected to the fluorescent activated cell analysis, using different combinations of human lineage reactive antibodies that were not reported to be expressed on any melanomas (CD45/Ter119), and specific candidate MSC markers. After performing multiple stains of melanoma cells with antibodies to the previously described antigens, it was found that CD271 was the most robust and reliable molecule in distinguishing heterogeneous populations within melanoma cell mass independent of the location and stage of this disease (Table 1). CD271 was found to be heterogeneously expressed in 13 out of 15 melanomas analyzed compromising from ~2.5% to ~41% (mean=16.7%) of the total cell population.

In order to assess the presence of melanoma tumorigenic stem cells, we assayed a broad spectrum of melanomas by an in-vivo transplantation assay using immunocompromised mice lacking B-, T- and NK cell subsets ($Rag2^{-/-}\, \gamma c^{-/-}$ mice) as recipients, and adding matrigel (30%) to all of the inoculated cell fractions. To avoid factors that select for the most aggressive tumor subsets during in vivo or in vitro passaging, our cells were isolated directly from surgical patient samples and purified by FACS.

$CD271^+$ and $CD271^-$ cell populations were fractionated to a high degree of purity, then mixed with matrigel and injected intradermally into $Rag2^{-/-}\, \gamma c^{-/-}$ mice at various cell doses. In parallel, the lineage negative cell population ($CD45^-$ $Ter-119^-$) was fractionated at the same time by FACS and injected into matching mice.

Strikingly, we found that the CD271+ cell population isolated directly from six different patients initiated melanomas at a dramatically higher rate when compared to $CD271^-$ or $Lin^-$ cells obtained from the same tumor. In doses ranging from 10 to 100K cells, CD271+ cells engrafted in 67.6% (25/37) of the transplants compared to 7.5% (3/40) of $CD271^-$ and 15.6% (5/32) of $Lin^-$ cells.

Some primary site melanomas were too small to study, and in these small pieces of freshly resected tumors were transplanted subcutaneously onto the back of $Rag2^{-/-}\, \gamma c^{-/-}$ mice. These first passage tumor xenografts (n=7) were then processed to obtain single cell suspensions and tumorigenic transplantation assays were performed as described above. CD271+ expression in xenografted tumors varied from 6.4% to 75.3% (mean=26.3%) of the total cell population. The CD271+ population engrafted growing melanomas in 82% of CD271+ cell injections (23/28) compared to 18.7% tumor engraftment from $CD271^-$ cells (3/16).

We wished to determine whether newly identified MTSCs were capable of self-renewal and differentiation in vivo. First, we analyzed engrafted melanomas derived from $CD271^+$ cells. All but one tumor redeveloped both $CD271^+$ and $CD271^-$ cell populations, with similar proportions of positive and negative cells compared to the cancer samples from which they were initially purified.

We tested whether the $CD271^+$ and/or the $CD271^-$ from xenografts representing two different patients were able to serially transplant melanoma in vivo; 72.2% (13/18) of the samples of $CD271^+$ cells engrafted growing melanomas compared to 27.7% (5/18) for $CD271^-$ in cell doses ranging from 10 to 5K injected cells.

In summary, these experiments provided convincing arguments that in most patients melanoma cancer stem cells reside in the $CD271^+$ fraction as they are able to not only induce tumors but to re-establish the original CD271 expression heterogeneity of the primary site cancers.

The in vivo melanoma transplantation assays demonstrated that $CD271^+$ cells engrafted in ~75% (64/86), while $CD271^-$ engrafted only in ~16% (13/78) and required much higher cell doses to induce tumor formation.

In order to test whether human skin provided a more physiologically relevant environment, we created a human-mouse skin chimeras by grafting pieces of human skin onto the back of immunocompromised mice. These humanized mice were used to further assess tumorigenic potential of $CD271^+$ cells. A dermal melanoma xenograft derived from a patient diagnosed with a primary skin lesion was used to purify $CD271^+$ and $CD271^-$ melanoma cells as described above. 20,000 cells of highly purified cell fractions were injected into the human skin of chimeric mice. After 7 months the $CD271^+$ cells induced a large tumor in the human skin, while no tumor growth was observed at the site injected with $CD271^-$ cells.

We repeated the human skin chimera experiment with a melanoma obtained directly after tumor resection. A dermal skin melanoma was sorted as above into cell fractions of $CD271^+$ and $CD271^-$ cells, which were injected into the human skin of the human-mouse graft chimeric $Rag2^{-/-}\, \gamma c^{-/-}$ mice at the doses of 6,000 and 20,000 respectively. Four weeks later the site of human skin injected with $CD271^+$ cells developed a neoplastic lesion. Upon examining both human transplants injected with $CD271^+$ and $CD271^-$ cells it can be clearly demonstrated that only $CD271^+$ cells induced melanoma formation in human skin, while no neoplastic growth can be detected in the human skin transplant injected with $CD271^-$ cells at a cell dose 3 times higher (20,000). Furthermore, analysis of lung tissues from both mice revealed that the tumor induced by $CD271^+$ melanoma cells in the human skin had metastasized into the lungs and caused formation of pulmonary metastatic nodules. In vivo intradermal tumorigenic assays of additional metastatic melanomas have demonstrated that in two more independent cases, tumors formed by $CD271^+$ cells had the ability to form metastases in the lung and liver. These results show that $CD271^+$ melanoma cancer stem cells contain a metastatic tumor initiation population.

We tested whether additional hierarchies exist within $CD271^+$ melanoma cancer stem cells. Previous reports indicate that CD146/MCAM and CD133 can regulate melanoma progression and development. FACS analysis of single cell suspensions of multiple melanoma samples revealed that $CD271^+$ MTCSs can in fact be further refined with the above markers. Single cell suspensions were prepared from freshly resected tumor and from xeno-implanted samples representing two different patients diagnosed with primary cutaneous melanoma; these were sub-fractionated with CD271/CD146 or CD271/133 markers by FACS. Tumorigenic assays in RAG/G DKO clearly indicated that melanoma cancer stem cell populations can reside within $CD271^+/CD146^+$; $CD271^+/CD133^+$ cells.

Pioneering studies of T cell immunity to melanoma antigens has led to immunotherapy trials. Multiple immunotherapies based on the well defined melanoma antigens (MART-1, Tyrosinase, HMB-45, gp100) have had limited success in treating melanoma patients. Immunostaining of $CD271^+$ cells with these antigens in this study demonstrates that the $CD271^+$ cells driving melanoma progression lack expression of those markers, and in our samples only a subset of CD271 cells express the MAGE marker. In addition expression of Ki67 is also greatly reduced in MTSCs, explaining failure of current chemotherapies (targeting highly proliferative cells) to completely eradicate this tumor.

In this study the neural crest stem cell marker CD271, was implicated as a cancer stem cell marker, allowing identification and prospective isolation of melanoma cancer stem cells.

Previous studies on human melanoma have found few candidate markers that unequivocally identify within the tumor a cancer stem cell population. A study of melanoma using principally metastatic tumors or tumors passaged by xenografts in mice revealed by limiting cell transfers, including single cell transfers, frequencies of ~1 in 3 to 1 in 6 cells that are tumor initiating when transplanted into NOG mice in matrigel. This study has popularly

|  | 10-100 | | 1000-2000 | | 3,000-10,000 | | 20,000-100,000 | |
| --- | --- | --- | --- | --- | --- | --- | --- | --- |
|  | − | + | − | + | − | + | − | + |
| Surgical Samples | 0/10 | 3/10 (P < 0.033) | 1/18 | 16/18 (P < 0.0001) | 2/9 | 6/8 (P < 0.015) | 0/3 | NA | been characterized as showing that in melanoma there are no cancer stem cells; asserting that all cells in a cancer are equally tumorigenic, and has been used to cast doubt on all other data in the field showing the existence of a tumorigenic cancer stem cell subset. Our data, which is based on a number of primary melanomas and highly stringent conditions of cell purity isolation imposed by FACS, contradicts those conclusions. We show that a tumor hierarchy exists within a number of melanoma sub-types and those tumors are being driven by $CD271^+$ melanoma cancer stem cells, and that in these cancers $CD271^+$ cells are the

|  | 10-100 | | 1000-2000 | | 3,000-10,000 | | 20,000 | |
| --- | --- | --- | --- | --- | --- | --- | --- | --- |
|  | − | + | − | + | − | + | − | + |
| Xenograft Samples | 4/14 | 9/14 (P < 0.031) | 3/13 | 20/24 (P < 0.0001) | 3/10 | 9/10 (P < 0.0021) | 0/1 | 1/1* | precursors of $CD271^-$ non-tumorigenic progeny.

Melanomas are extremely aggressive tumors and can undergo tumorigenic evolution towards more malignant stages. Our data is consistent with the possibility that some metastatic melanomas have very high frequencies of CSC, and that transfer of melanomas in mice or in vitro passaging in cell culture can result in emergence of the most carcinogenic clones with a reduced frequency of differentiated, non-tumor initiating cells.

TABLE 1

Summary of $CD271^{P75(NGFR)}$ tumor engraftment (Surgical Samples)
Total:

| Lin− | 5/29 | (~17.2%) |
| --- | --- | --- |
| CD271− | 3/40 | (~7.5%) |
| CD271+ | 25/37 | (~67.5%) |

TABLE 2

Summary of $CD271^{P75(NGFR)}$ tumor engraftment (Xenograft Samples)
Total:

| CD271− | 10/38 | (~26%) |
| --- | --- | --- |
| CD271+ | 39/49 | (~80%) |

(!) metastatic lesions; (*) humanized mouse system
(P0) surgically removed patient's tumor implanted into RagDKO mice TABLE 2-continued (P1) patient's tumor serially passaged in RagDKO mice
(Pi) surgically removed patient's tumor expanded in-vitro and injected into RagDKO mice

| Total of all melanoma samples: | Lin− | 5/29; | (~17.2%) |
| --- | --- | --- | --- |
|  | CD271− | 13/78; | (~16.6%) |
|  | CD271+ | 64/86 | (~74.4%) |

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. Moreover, due to biological functional equivalency considerations, changes can be made in protein structure without affecting the biological action in kind or amount. All such modifications are intended to be included within the scope of the appended claims.

What is claimed is:

1. A method for characterizing a melanoma from a human patient, the method comprising:
    contacting a sample of melanoma cells with a reagent specific for CD271; with a reagents specific CD47, and with a reagent specific for CD133;
    quantitating the number of $CD271^+ CD47^+ CD133^+$ cancer cells in the sample, which $CD271^+ CD47^+ CD133^+$ cells are melanoma stem cells by flow cytometry or immunohistochemistry;
    characterizing the sample, wherein a greater number of $CD271^+ CD47^+ CD133^+$ melanoma stem cells in the sample is indicative of a characterization as a more aggressive cancer phenotype; and
    providing the characterization to the patient.

2. The method of claim 1, further comprising contacting the sample of melanoma cells with a reagent specific for one or more of MART-1, tyrosinase, HMB-45, and gp100, and quantitating cells that are $CD271^+ CD47^+ CD133^+$ and negative for expression of MART-1, tyrosinase, HMB-45, and gp100, which cells are melanoma stem cells.

3. The method of claim 1, wherein the sample is a biopsy sample.

4. The method of claim 1, wherein the patient has been diagnosed as having melanoma.

5. The method of claim 4, wherein the patient is undergoing treatment for melanoma.

6. A method for purification of a melanoma cancer stem cell, the method comprising
    contacting a sample of melanoma cells with a reagent specific for CD271; with a reagents specific CD47 and with a reagent specific for CD133;
    selecting for $CD271^+$, $CD133^+$, $CD47^+$ cancer cells.

7. The method of claim 6, further comprising contacting the sample of melanoma cells with a reagent specific for one or more of MART-1, tyrosinase, HMB-45, and gp100; and selecting for cells that lack expression of at least one of MART-1, tyrosinase, HMB-45, and gp100.

8. A method for the treatment of melanoma in a subject in the need thereof, said method comprising the step of administration of an effective amount of an antibody that selectively binds to or inhibits CD271.

9. The method according to claim 8, wherein said antibody also selectively binds one or both of CD47 and CD133.

10. The method according to claim 8 wherein the antibody that selectively binds CD271 is an antibody comprising human IgG1 constant region sequences, and which binds via the Fc region to the FcRII on macrophages and NK cells.

11. The method according to claim 8, said method further comprising the step of administration of an effective amount of an antibody that selectively binds to or inhibits CD47.

12. The method according to claim 9, wherein said method provides for phagocytosis and death of melanoma cancer stem cells.

13. The method of claim 8, wherein said antibody is a bivalent and monospecific antibody.

14. The method of claim 8, wherein the antibody is a bivalent and bispecific antibody.

15. The method of claim 13, further comprising the step of administration of an effective amount of an agent that selectively binds to or inhibits CD47, wherein said agent is a bispecific or monospecific antibody, or soluble Sirp alpha.

\* \* \* \* \*